United States Patent
Palermo

(12) 
(10) Patent No.: US 6,656,173 B1
(45) Date of Patent: Dec. 2, 2003

(54) METHOD AND DEVICE FOR ENHANCING VESSEL OCCLUSION

(75) Inventor: Thomas Palermo, San Jose, CA (US)

(73) Assignee: Radio Therapeutics Corporation, Mountain View, CA (US)

( * ) Notice: Subject to any disclaimer, the term of this patent is extended or adjusted under 35 U.S.C. 154(b) by 0 days.

(21) Appl. No.: 09/845,774

(22) Filed: Apr. 30, 2001

Related U.S. Application Data

(63) Continuation of application No. 08/605,765, filed on Feb. 22, 1996, now Pat. No. 6,270,495.

(51) Int. Cl.[7] .............................................. A61B 18/04
(52) U.S. Cl. .......................................... 606/32; 606/51
(58) Field of Search ............................ 606/41–52, 157, 606/158

(56) References Cited

U.S. PATENT DOCUMENTS

| | | |
|---|---|---|
| 1,814,791 A | 7/1931 | Ende |
| 1,908,583 A | 5/1933 | Wappler |
| 1,943,543 A | 1/1934 | McFadden |
| 1,995,526 A | 3/1935 | Wappler |
| 2,022,065 A | 11/1935 | Wappler et al. |
| 3,100,489 A | 8/1963 | Bagley |
| 3,868,956 A | 3/1975 | Alfidi et al. |
| 4,005,714 A | 2/1977 | Hiltebrandt |
| 4,011,872 A | 3/1977 | Komiya |
| 4,041,952 A | 8/1977 | Morrison, Jr. et al. |
| 4,209,018 A | 6/1980 | Meinke et al. |
| 4,341,218 A | 7/1982 | U |
| 4,492,231 A | 1/1985 | Auth |
| 4,582,057 A | 4/1986 | Auth et al. |
| 4,655,216 A | 4/1987 | Tischer |
| 4,685,459 A | 8/1987 | Koch et al. |
| 4,994,069 A | 2/1991 | Ritchart et al. |
| 5,108,407 A | 4/1992 | Geremia et al. |
| 5,122,136 A | 6/1992 | Guglielmi et al. |
| 5,217,484 A | 6/1993 | Marks |
| 5,226,911 A | 7/1993 | Chee et al. |
| 5,234,437 A | 8/1993 | Sepetka |

(List continued on next page.)

FOREIGN PATENT DOCUMENTS

| | | |
|---|---|---|
| DE | 25 40 968 | 3/1977 |
| DE | 26 46 228 | 4/1978 |
| DE | 41 39 029 | 6/1993 |
| JP | 2-121675 | 5/1990 |
| WO | WO 93/01758 | 2/1993 |
| WO | WO 93/06884 | 4/1993 |
| WO | WO 94/06503 | 3/1994 |
| WO | WO 94/09705 | 5/1994 |
| WO | WO 94/10936 | 5/1994 |
| WO | WO 94/11051 | 5/1994 |
| WO | WO 95/02366 | 1/1995 |

OTHER PUBLICATIONS

Becker et al., "Catherter for Endoluminal Bipolar Eletrocoagulation", 1989, *Radiology*, vol. 170, pp. 561–562.

Becker et al., "Long–Term Occlusion of the Porcine Custic Duct by Means of Endoluminal Radio–Frequency Electrocoagulation", 1988, *Radiology*, vol. 167, pp. 63–68.

(List continued on next page.)

Primary Examiner—Linda C. M. Dvorak
Assistant Examiner—Peter J Vrettakos
(74) Attorney, Agent, or Firm—Bingham McCutchen LLP

(57) ABSTRACT

Body lumens such as blood vessels are selectively occluded by applying radiofrequency voltage to a vaso-occlusive coil (100) at the target site (TS) and generating a thermal reaction to induce fibrogenic occlusion of the blood vessel (BV) around the vaso-occlusive coil. The radiofrequency current is usually sufficient to induce thermal damage to the luminal wall and to coagulate the surrounding blood, thereby initiating clotting and subsequent fibrosis to permanently occlude the lumen. The invention also includes a method for endoluminally deploying the vaso-occlusive coil and preventing migration of the coil from of the target site.

19 Claims, 6 Drawing Sheets

U.S. PATENT DOCUMENTS

| | | | |
|---|---|---|---|
| 5,236,410 A | | 8/1993 | Granov et al. |
| 5,250,071 A | | 10/1993 | Palermo |
| 5,261,916 A | | 11/1993 | Engelson |
| 5,281,216 A | | 1/1994 | Klicek |
| 5,312,415 A | | 5/1994 | Palermo |
| 5,350,397 A | | 9/1994 | Palermo et al. |
| 5,354,295 A | | 10/1994 | Guglielmi et al. |
| 5,364,939 A | | 11/1994 | Roduit |
| 5,366,490 A | | 11/1994 | Edwards et al. |
| 5,385,544 A | | 1/1995 | Edwards et al. |
| 5,405,322 A | | 4/1995 | Lennox et al. |
| 5,569,245 A | | 10/1996 | Guglielmi et al. |
| 5,626,578 A | * | 5/1997 | Tihon .................. 606/48 |
| 5,810,764 A | * | 9/1998 | Eggers et al. .......... 606/41 |
| 6,019,757 A | * | 2/2000 | Scheldrup ............. 606/49 |

OTHER PUBLICATIONS

Brunelle et al., "Endovascular Electrocoagulation with a Bipolar Electrode and Alternating Current: A Follow–up Study in Dogs", 1983, *Radiology*, vol. 148, pp. 413–415.

Cragg et al., "Endovascular Diathermic Vessel Occlusion", 1982, *Radiology*, vol. 144, pp. 303–308.

Grant Application, Department of Health and Human Services, Public Health Service, From the Regents of University of California, 405 Hilgard Avenue, Los Angeles, CA. 58 pages total.

Tanigawa, N. et al., "Interaarterial Occlusion By Radiofrequency", 1994, *Acta Radiological*, ISSN 0248–1851, pp. 626–628.

* cited by examiner

METHOD AND DEVICE FOR ENHANCING VESSEL OCCLUSION

This application is a continuation of U.S. patent application Ser. No. 08/605,765, filed Feb. 22, 1996, now issued as U.S. Pat. No. 6,270,495, the entire disclosure of which is expressly incorporated by reference herein.

BACKGROUND OF THE INVENTION

1. Field of the Invention

The present invention relates generally to methods and devices for the selective occlusion of body lumens. More particularly, the present invention relates to methods and devices for applying high frequency electrical energy to vaso-occlusion elements within the body lumen to enhance fibrogenic occlusion of the body lumen.

The selective occlusion of blood vessels in a patient is a part of many modem therapeutic treatments, including the control of internal bleeding, the occlusion of blood supply to tumors, the isolation of diseased body organs prior to removal, the relief of blood pressure in a region of aneurism, and the like. While such procedures rely generally on the blockage of arteries, the selective occlusion of veins is also useful in procedures such as veiniotomy.

The selective occlusion of blood vessels can be achieved by a variety of specific techniques. One such technique involves mechanically clamping or occluding the target site within the blood vessel. For example, in open surgical and endoscopic procedures, the body vessel can be externally clamped and radiofrequency energy applied. While the external procedures can be very effective, it requires external access to the lumen and is unsuitable for endoluminal techniques.

Mechanical endoluminal techniques for selective vessel occlusion are also in use. Such techniques include the use of detachable balloons, embolic and vaso-occlusion coils, and the like to physically block the vessel lumen. Detachable balloons are typically advanced to the vessel site at the end of a catheter and inflated with a suitable fluid, such as saline, x-ray contrast or a polymerizable resin, and released from the end of the catheter. These detachable balloons, however, are difficult to deliver and may not be suitable for permanent implantation unless they are used with the polymerizable resin. In addition, the catheter or the balloon can rupture or release prematurely during filling, leaking monomer resin into the vasculature.

Embolic or vaso-occlusion coils are typically introduced through a catheter in a stretched linear form, and assume a relaxed, helical shape when released into a vessel. One of the limitations of these coils is that recanalization of the occlusion site can occur when the initial blood clot is broken down by the body's natural anticoagulant mechanism (i.e., resorption of the clot). In addition, once the embolic coils are released by the introducer catheter, they are no longer under control and they frequently migrate from the point of initial implantation.

To completely arrest the flow of blood in a vessel and to inhibit recanalization, current methods of coil embolization typically require the use of several embolic coils at the target site in the blood vessel. In this "nesting technique", the embolic coils are deposited within a vessel to create a mechanical "plug". It has been found, however, that the use of several coils does not always prevent recanalization of the blood vessel, particularly in larger, high flow vessels. Moreover, it often takes a relatively long time for the blood vessel to completely occlude. Therefore, the embolic coils may often migrate into a non-target site prior to vessel occlusion, particularly in larger or high flow vessels. Multiple coils are also more expensive than a single coil and they require more time to position within the vessel, thereby further increasing the cost of the procedure and prolonging the patient's exposure to the fluoroscope.

Of particular interest to the present invention, the use of monopolar and bipolar radiofrequency devices has been proposed for the occlusion of body vessels from a surrounding lumen or body cavity. For example, U.S. Pat. No. 5,403,311 describes control of vessels bleeding into a body lumen using electrosurgical electrodes which puncture the vessel from within a larger lumen enclosing that vessel. Catheters for radiofrequency injury and occlusion of the cystic duct are described in Becker et al. (1989) *Radiology* 170:561–562 and (1988) *Radiology* 167:63–68 and Tanigawa et al. (1994) *Acta Radiologica* 35:626–628. Methods and catheters for electrosurgical endovascular occlusion are described in Brunelle et al. (1980) Radiology 137:239–240; Cragg et al. (1982) *Radiology* 144:303–308; and Brunelle et al. (1983) Radiology 148:413–415. Such techniques, however, have not generally been useful in large or high flow blood vessels.

For these reasons, it would be desirable to provide improved methods and devices for endoluminal occlusion of body lumens, and particularly of blood vessels, for use in the procedures described above. Such methods and devices should provide effective occlusion of large or relatively high flow body lumens as well as small body lumens. Preferably, the methods and devices will permit the physician to re-access the occlusion site, to correct recanalization and/or to enhance the occlusion of this site to prevent subsequent recanalization of the body lumen.

2. Description of the Background Art

Methods and devices for implanting vaso-occlusive elements, such as coils, in blood vessels and other lumen are described in U.S. Pat. Nos. 5,354,295; 5,350,397; 5,312,415; 5,261,916; 5,250,071; 5,234,437; 5,226,911; 5,217,484; 5,122,136; 5,108,407; '4,994,069; and 3,868,956; and published PCT applications WO 94/11051; WO 94/10936; WO 94/09705; WO 94/06503; and WO 93/06884. Some of the devices described in the above listed patents and published applications suggest passing direct current through the element to enhance blood clotting.

Electrosurgical probes for electrosurgical, electrocautery, and other procedures are described in U.S. Pat. Nos. 5,405,322; 5,385,544; 5,366,490; 5,364,393; 5,281,216; 5,236,410; 4,685,459; 4,655,216; 4,582,057; 4,492,231; 4,209,018; 4,041,952; 4,011,872; 4,005,714; 3,100,489; 2,022,065; 1,995,526; 1,943,543; 1,908,583; and 1,814,791; and published Japanese application 2-121675; published German applications DE 4139029; DT 2646228; and DT 2540968; and published PCT applications WO 95/02366 and WO 93/01758.

A method and system employing RF energy for the direct occlusion of blood vessels and other body lumens are described in co-pending application Ser. No. 08/488,444 filed on Jun. 7, 1995 (attorney docket No. 16807-3), the full disclosure of which is incorporated herein by reference. See also the patent and publications described in the Field of the Invention above.

SUMMARY OF THE INVENTION

Methods and apparatus are provided for deploying vaso-occlusive elements into body lumens, such as blood vessels, to occlude a target site within the lumen and for enhancing the occlusion of body lumens that already have vaso-occlusive elements deployed therein. The technique involves applying high frequency electrical energy to an electrically conductive, vaso-occlusive element and generating a thermal reaction at the target site to damage the luminal wall and induce fibrogenic occlusion of the blood vessel around the vaso-occlusive element. The vaso-occlusive element, which is typically an electrically conductive wire coil, helps reduce blood flow within the vessel and provides a larger surface for energy transfer between the electrical energy source and the tissue wall and surrounding blood. The high frequency electrical energy, typically radiofrequency current, is usually sufficient to induce local heating of the luminal wall and also to enhance coagulation of the surrounding blood, thereby initiating clotting. The thermally injured wall then contributes to subsequent fibrosis, thus permanently occluding the lumen.

The vaso-occlusive coil typically has a relatively low electrical resistance so that the high frequency electrical energy flows directly through the vaso-occlusive coil to the luminal wall (i.e., without substantially heating the coil). The electrical energy heats the luminal wall, thereby causing damage and subsequent fibrogenic occlusion of the target site. Alternatively, the vaso-occlusive coil may comprise sufficient electrical resistance such that a portion of the high frequency electrical energy is transferred directly to the coil (rather than the luminal wall) to heat the coil and enhance occlusion around the coil. In this case, the vaso-occlusive coil will preferably have an electrical resistance slightly less than the tissue wall to ensure that the electrical energy flows through at least a substantial portion of the coil.

In one aspect, the method comprises contacting a vaso-occlusive coil that is already deployed at a target site within a body lumen with at least one electrode and applying the high frequency electrical energy to the coil in a monopolar or bipolar fashion. Preferably, the energy is applied in a monopolar mode by contacting the patient's body with a second, dispersive or return, electrode and then delivering a high frequency current to the first or active electrode, through at least a portion of the vaso-occlusive coil, the surrounding tissue, and finally to the second electrode. For bipolar operation, a separate second electrode may be provided on the catheter, typically spaced proximally from the first electrode so that it will be located within the body lumen. The second electrode will usually be spaced a distance of about 2 mm to 10 cm from the active electrode.

The first electrode will usually be disposed on the distal end of an intravascular catheter. The catheter can be percutaneously introduced via well-known procedures and advanced to the target site in a body lumen in a known manner, typically over a guide wire. The first electrode can be engaged against the vaso-occlusive coil in a variety of ways. For example, the electrode (and optionally a pair of electrodes for bipolar operation) can simply be disposed at a distal location on the catheter which will contact the vaso-occlusive coil when the catheter is advanced through the body lumen to the target site.

Alternatively, the electrode may be provided by a separate member, such as an insulated conventional or specialized guide wire, or a positioner device, which may be insulated by the catheter body. In use, the guideline positioner is extended distal to the catheter body, placed against the vaso-occlusive coil, and the radiofrequency current is applied thereto. In the latter case, a distal portion of the positioner may comprise the active electrode, while the return electrode is located on the catheter or placed externally on the patient.

In other aspects, the method may comprise deploying the vaso-occlusive coil at the target site within the body lumen, adjusting the position of an already deployed vaso-occlusive coil within the target site, or repositioning the coil to another location in the vasculature. For initial deployment, the vaso-occlusive coil will be releasably engaged by the positioner and optionally advanced through the axial lumen of the catheter for deployment. For repositioning, the coil may be captured by the positioner and partially or fully retracted into the axial lumen for adjusting coil placement or repositioning the coil to another location. Typically, the coil will be repositioned when previous attempts to occlude a target site have not completely succeeded and the coil is not fixed at the site. A particular advantage of the present invention is that the coil can be held in place within the body lumen by the positioner until the high frequency voltage or current has been applied thereto. Once the voltage has generated a sufficient thermal reaction to induce spasm and localized edema/narrowing of the vessel (and subsequent fibrogenic occlusion of the lumen) around the coil, the coil will be released from the positioner and the positioner removed from the vasculature. In this manner, the fibrogenic occlusion of the blood vessel will slowly and permanently lock the coil in position at the occlusion site, while the coil is temporarily held in place by the spasm or narrowing of the vessel. This prevents or at least inhibits migration of the coil downstream through the body lumen after it has been released by the positioner.

Devices according to the present invention will generally comprise a shaft having proximal and distal ends and an axial lumen therebetween. For vascular applications, the shaft will typically be a non-conductive, tubular catheter body capable of being introduced to the vascular system over a guide wire in a conventional manner. A positioner is slidably disposed within an axial lumen of the shaft and includes a first electrode at the distal end for contacting the vaso-occlusive coil. The positioner may be a guide wire that is also used for advancing the shaft through the body lumen or a separate device inserted into the catheter body after it has been advanced to the target site. The first electrode is coupled to a source of high or radiofrequency electrical energy by the positioner itself, an electrical conductor extending through the positioner, or through the catheter body.

The positioner preferably comprises a conductive shaft having an outer insulating sheath extending to a distal portion of the shaft. The distal portion includes an engaging element for releasably engaging the vaso-occlusive coil to either deploy the coil at the target site or to reposition a deployed coil to another location in the patient's vasculature. In one embodiment, the engaging element comprises a pair of opposed elements which can be selectively opened and closed to engage and release a proximal portion of the coil. Usually, the opposed elements will be openable jaws that are actuated manually with an actuator located on a handle at the proximal end of the positioner. In another embodiment, the distal engaging element comprises a plurality of resilient hooks that are biased away from each other and held together by the catheter body. In yet another embodiment, the distal engaging element comprises a distal pusher element adapted to contact the coil and push it through the catheter body to the target site.

The system of the present invention will also include a second electrode operatively coupled to the high frequency energy source. The second electrode can be either a second bipolar electrode disposed on the positioner (usually spaced proximally from the first electrode), the catheter, or introducing sheath, or a dispersive or return electrode attachable directly to the patient's skin (where the first or active electrode will function in a monopolar manner). The electrodes are thus utilized to apply monopolar or bipolar high frequency energy to the vaso-occlusive coil within the vessel lumen. For example, a separate guide wire could be provided as either a monopolar or one bipolar electrode.

Frequently, the first electrode(s) will be associated with the distal engaging elements. For example, the opposing jaws or the resilient hooks can also define the treatment electrodes on the positioner. In the bipolar mode, most likely, a separate, second radiofrequency electrode can be provided on the catheter.

BRIEF DESCRIPTION OF THE DRAWINGS

FIGS. 3A–3D illustrate the use of the system of FIG. 1 and a method for enhancing occlusion of a blood vessel according to the principles of the present invention;

DESCRIPTION OF THE SPECIFIC EMBODIMENTS

Figure 1:
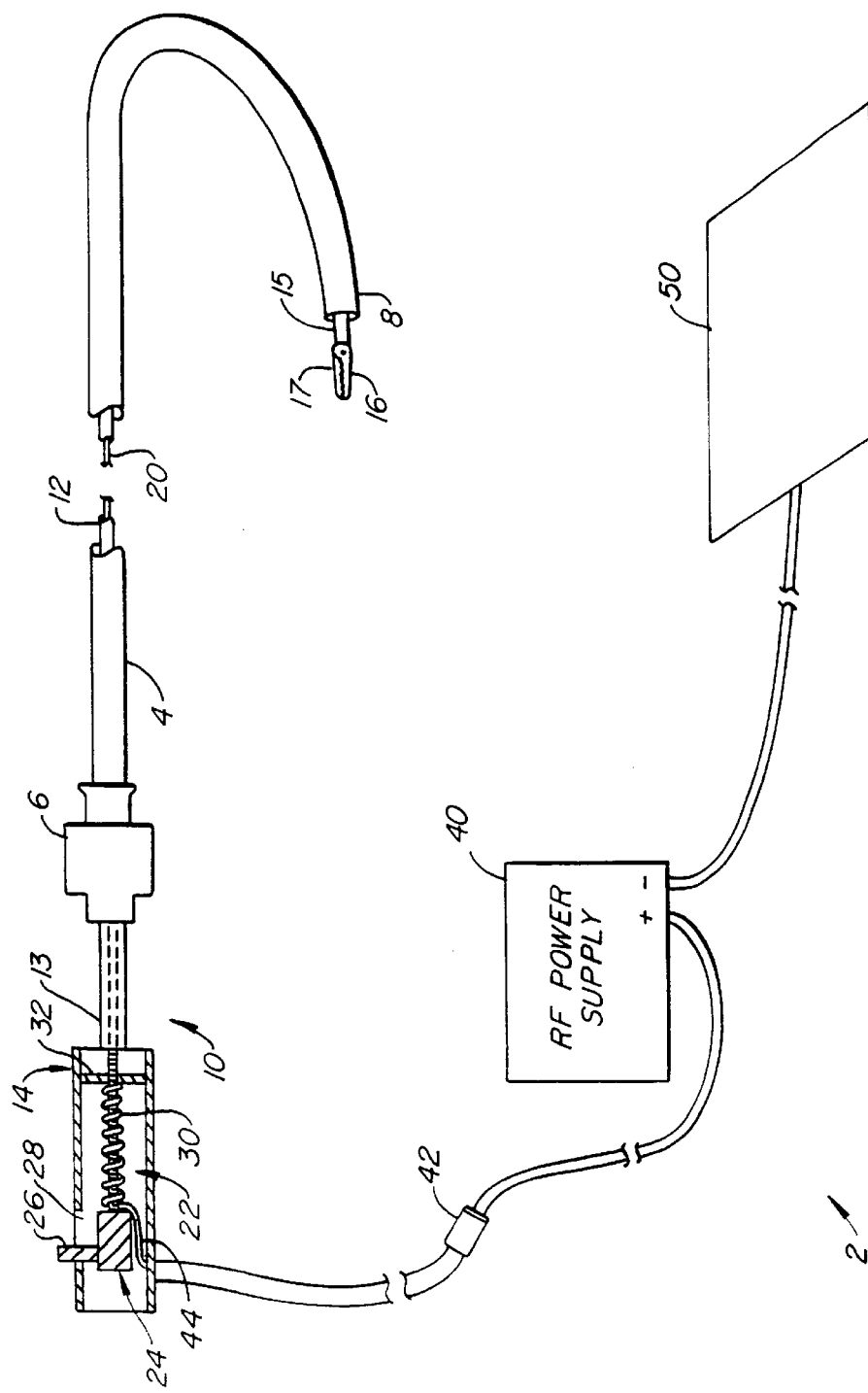
FIG. 1 is a schematic view of a lumen occlusion system constructed in accordance with the principles of the present invention.

The methods and devices of the present invention will be useful for selectively occluding virtually any body lumen that can be occluded with a vaso-occlusive element(s) followed by the application of energy. While the present invention will find its greatest use in the selective occlusive of blood vessels, including both arteries, veins, fistulas and aneurysms, it will also find use with other body lumens, such as the fallopian tubes, bile ducts, and the like. The present invention will be particularly useful for occluding relative large, high flow arteries, veins and vascular malformations, because the present invention presents a method of releasably holding a vaso-occlusive element(s) until the target site of the fluid vessel is partially or completely occluded. In high flow vessels, this effectively prevents the vaso-occlusive element(s) from becoming dislodged and migrating downstream of the target site.

In the case of blood vessel occlusion, the high frequency electrical energy will coagulate surrounding fluids, such as blood, and thermally injure the intima of the body luminal wall in the occlusion region, thus initiating a process of thrombosis and fibrosis which will result in relatively complete vessel occlusion. The high frequency electrical energy passes through the vaso-occlusive element, which usually takes the form of an electrically conductive coil, into the body luminal wall. The electrical energy heats the luminal wall, thereby enhancing the thrombogenic and fibrogenic occlusion of the coil at the target site. The vaso-occlusive coil typically has a relatively low electrical resistance so that the high frequency electrical energy flows directly through the coil to the luminal wall and surrounding fluid (in fluid carrying vessels) without substantially heating the coil. The electrical energy heats the body luminal wall, creating a thermal effect and thereby causing damage and subsequent fibrogenic occlusion of the target site. The temperature of the luminal wall will be typically be raised to about 45° C. to 95° C., preferably about 55° C. to 85° C.

Alternatively, the vaso-occlusive coil may comprise a material having some electrical resistance so that a portion of the high frequency electrical energy heats the vaso-occlusive coil. In this case, the coil will preferably have an electrical resistance less than the tissue wall to ensure that the electrical energy flows through at least a substantial portion of the coil.

Preferably, the energy source will provide radiofrequency electrical energy, such as that supplied by conventional electrosurgical power supplies, such as those available from commercial vendors, including Valleylab®, Aspen®, Bovie®, and Birtcher®. The power supply will usually provide energy at frequencies from 200 kHz to 12 MHz, preferably from 250 kHz to 500 kHz and may employ a conventional sinusoidal or non-sinusoidal wave form. The current provided will usually be in the range from about 25 mA to 1 A, preferably from about 50 mA to 250 mA from about 5 seconds to 4 minutes, usually from 10 seconds to 1 minute. The actual amplitude and duration of the current will depend primarily on vessel size, i.e. larger vessels will usually require higher currents and longer durations.

As discussed in more detail in connection with the specific embodiments below, the RF current may be applied in a monopolar or a bipolar fashion in or near the occlusion region. By "monopolar" it is meant that current flow will pass between (1) one or more "active" electrodes on the introducing catheter or the positioner which have surface areas and configurations which transfer the energy to the vaso-occlusive coil in order generate a thermal reaction in the region of the target site; and (2) a "dispersive" or return electrode which is located remotely from the active electrode(s) and which has a sufficiently larger area so that the current density is low and non-injurious to surrounding tissue. In some cases, the dispersive electrode may be on the same probe as the active electrode, and in other cases, the dispersive electrode may be attached externally to the patient, e.g., using a contact pad placed on the patient's flank.

Bipolar devices according to the present invention will generally employ a pair of electrodes in relatively close proximity each having an area and geometry selected to have a desired physiologic effect on adjacent tissue. In the case of bipolar devices, one or more electrodes will be connected to one pole of the radiofrequency power supply and will be placed in contact with the vaso-occlusive coil. The other electrode will be directly or indirectly in contact with the body luminal wall. Thus, the current flow in the occlusion region will be concentrated through the vaso-occlusive coil, then through the luminal wall or through the fluid located between electrode pair(s), rather than from one or more electrodes to a remote, dispersive electrode (which is the case in monopolar operation).

Devices according to the present invention will comprise an introducing catheter, typically including a shaft having proximal and distal ends and an axial lumen therebetween. For vascular applications, the shaft may be in the form of a conventional catheter body, typically having a length in the range from 40 cm to 200 cm, usually from 75 cm to 120 cm. The catheter body will usually include means for introducing the body over a movable guide wire, typically having a guide wire lumen running through at least a distal portion of the catheter body. Thus, the catheter body can have either conventional "over-the-wire" design where a movable guide wire is received through the entire length of the catheter body or may have a "rapid exchange" or "monorail" design where the guide wire is received through a lumen which extends only over a distal length of the body, typically from 5 cm to 25 cm. The catheter body will have an outside diameter consistent with its intended use, typically being from 1 mm to 5 mm, usually from 2 mm to 4 mm.

The catheter body may be formed from a variety of conventional catheter materials, including natural and synthetic polymers, such as polyvinyl chloride, polyurethanes, polyesters, polyethylenes, polytetrafluoroethylenes (PTFE's), nylons, and the like. The catheter bodies may optionally be reinforced to enhance their strength, torqueability, and the like. Exemplary reinforcement layers include metal fiber braids, polymeric fiber braids, metal or fiber helical windings, and the like. Optionally, a portion of the catheter body could be formed from a metal rod or hypo tube, particularly when the catheter body is a rapid exchange or monorail design.

The catheter will also include at least one electrode for initiating radiofrequency current flow, as described above. The electrode may be disposed on the catheter shaft, may be part of a separate positioner (described below), and/or may be associated with the guide wire used to introduce the shaft to the body lumen, usually a blood vessel. Configuration of the electrode element will vary depending on whether it is intended to actively contact the vaso-occlusive coil or to function as a return or dispersive electrode.

The dispersive electrode will typically have a substantially larger surface area, on the order of at least 2 to 3 times larger, than the active electrode. Active electrodes (the electrode and the occlusive coil) will typically have relatively small total surface areas, typically being below about 20 mm$^2$, usually being below about 10 mm$^2$. Dispersive electrodes will typically have a somewhat larger area, typically being greater than 50 mm$^2$ for probe-mounted dispersive electrodes and greater than 120 cm$^2$ for external dispersive pads.

The positioner will generally comprise a shaft that extends through the catheter body and includes a distal engaging element for releasably engaging a vaso-occlusive coil. The distal engaging element will also comprise the active electrode(s) (or one of a pair of electrodes in the bipolar mode). The engaging element will preferably comprise a holding or grasping mechanism that holds a proximal portion of the coil for deploying and/or repositioning the coil within a blood vessel. In this embodiment, the engaging element will be capable of holding onto the coil beyond the distal end of the catheter body and/or grasping an already deployed coil for establishing positive electrical contact between the engaging element and the coil, repositioning the coil or withdrawing the coil from the body lumen. Alternatively, the engaging element may comprise a mechanism for contacting the coil and pushing the coil through the catheter body. In this embodiment, the coil will generally disengage from the engaging element when its proximal end moves past the distal end of the catheter body. Electrical current may be re-established by subsequently advancing the positioner to contact the coil. Specific examples of each of these approaches are described in more detail in connection with the figures below.

The present invention will generally be useful with virtually any type of vasoocclusive device or coil that may be endoluminally advanced to a target site of a body lumen to block fluid passage therethrough. The vaso-occlusive device will typically be formed from an elongate element, such as a wire, which is extendable from a relaxed, convoluted condition, to an extended, linear condition in which the wire can be advanced through the catheter. The vaso-occlusive coil(s) will have a relatively large surface area compared to the electrode to facilitate transfer of the electrical energy to the tissue wall and surrounding blood. This surface area will usually depend on the size of the coil, which is typically chosen based on the size of the blood vessel. Larger vessels will typically require a higher rate of energy transfer due to a larger surface area.

The vaso-occlusive wire generally takes the form of a coil, and may be formed by wrappings or windings of a fine wire comprised of platinum, stainless steel, tungsten, gold or the like. The wire may be covered with a fibrous material, such as polyester, to induce thrombus in blood. The wire may be pre-formed so that it adopts a convoluted configuration in a relaxed condition. Alternatively, the vaso-occlusive device may be formed from a flexible pre-shaped polymer tube or rod that is doped with electrically conducting material so that the rod is more electrically conductive than the tissue of the body lumen. The convoluted shape of the tube or rod may be achieved by a combination of a helical winding and/or irregularities which are imparted during heat treatment, or by shaping the device as it is extruded, before cooling, or by injection molding.

Figure 2:
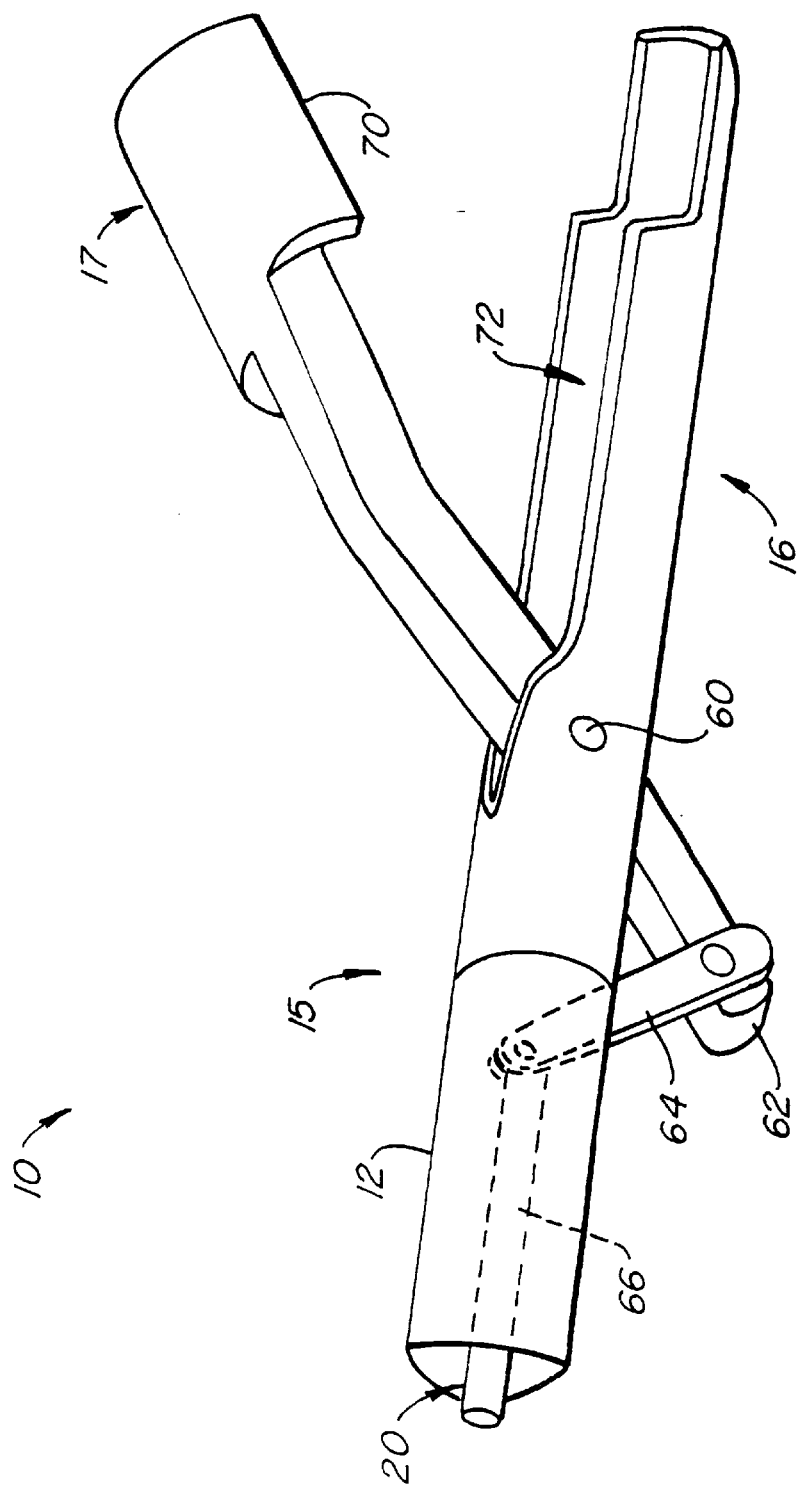
FIG. 2 is an enlarged perspective view of a distal end of a positioner device of the lumen occlusion system of FIG. 1, illustrating a pair of opposed elements shown in their open configuration.

Referring now to FIGS. 1–3, a lumen occlusion system 2 according to the present invention comprises a shaft in the form of a flexible catheter body 4 having a proximal end 6 and a distal end 8. A positioner 10 includes a flexible shaft 12 sized to extend through catheter body 4 and having a proximal end 13 attached to a handle 14. A pair of opposing elements or jaws 16, 17 are attached to a distal end 15 of flexible shaft 12 for movement between open and closed positions. Once catheter body 4 has been positioned within a blood vessel of the patient (discussed below), jaws 16, 17 may be introduced through proximal end 6 of catheter body 4 and advanced through distal end 8, as shown in FIG. 1.

Handle 14 includes an actuator mechanism for opening and closing jaws 16, 17. Preferably, the actuator mechanism comprises an inner rod 20 slidably disposed within shaft 12 and extending through an inner lumen 22 within handle 14. Rod 20 is coupled to a trigger 24 having a lever arm 26 extending through a slot 28 in handle 14. Distal movement of lever arm 26 through slot 28 moves rod 20 in the distal direction, causing jaws 16, 17 to open (see FIG. 2). A spring 30, positioned between a bushing 32 within lumen 22 and trigger 24, biases lever arm 26 proximally so that jaws 16, 17 are biased into the closed position (FIG. 1).

FIG. 2 illustrates a preferred embodiment of the distal end 15 of positioner 10.

As shown, jaws 16, 17 are pivotally coupled to each other by a pivot pin 60 extending through jaw 17. Jaw 17 has a proximal end portion 62 pivotally coupled to a linkage 64 which is, in turn, pivotally coupled to the distal end 66 of rod 20. Proximal movement of rod 20 withdraws linkage 64 into shaft 12, thereby pivoting proximal end portion 62 of jaw 17 toward shaft 12. In this manner, distal end portion 70 of jaw 17 is pivoted downward towards jaw 16 into the closed position (FIG. 1). Jaw 16 preferably has a recess 72 sized to receive jaw 17 to minimize the profile of positioner 10 in the closed position. Similarly, distal movement of rod 20 causes jaws 16, 17 to open (FIG. 2).

In this embodiment, jaws 16, 17 also serve as a common active electrode for providing radiofrequency current flow in a monopolar procedure. Referring again to FIG. 1, occlusion system 2 further comprises a suitable RF power supply 40 connected to handle 14 via a connection plug 42. Jaws 16, 17 are preferably coupled to connection plug 42 through inner rod 20 and a lead wire 44 within handle 14. Inner rod 20 may comprise an electrically conducting material or a lead wire (not shown) may extend through an inner lumen within rod 20. Positioner shaft 12 will be fabricated from an insulating material to insulate rod 20 from the patient. The occlusion system 20 further includes a dispersive or return electrode, which is an external dispersive plate 50 coupled to RF power supply 40 and adapted for mounting on the patient's skin. Of course, the dispersive electrode 50 could be located elsewhere in different form (e.g., a sleeve) on the catheter body 4.

Figure 3A:
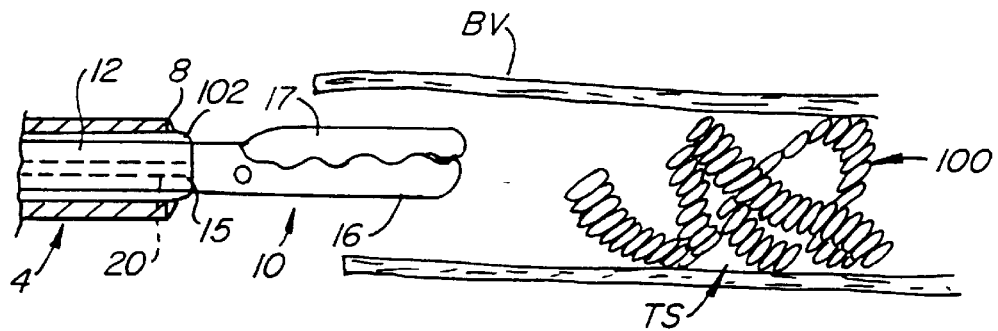
Figure 3B:
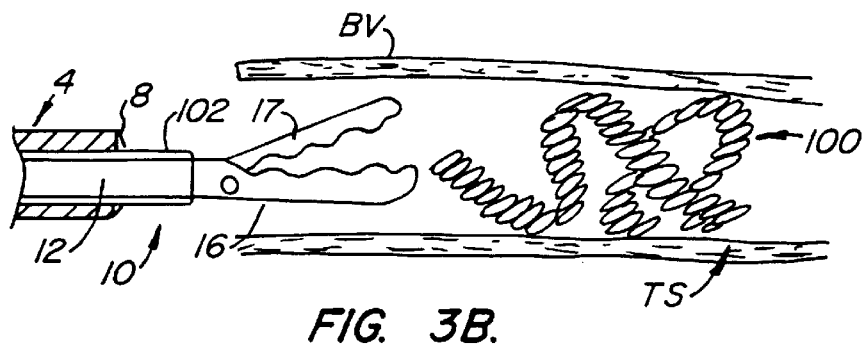
Figure 3C:
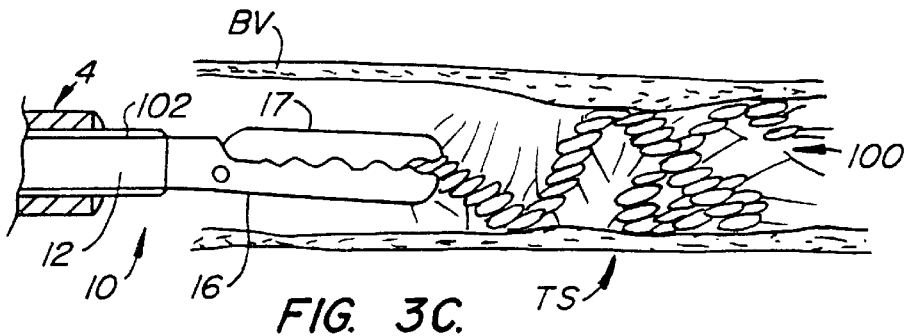

FIGS. 3A–3C illustrate use of the lumen occlusion system 2 to enhance occlusion of a target site TS within a blood vessel BV having one or more vaso-occlusive coils 100 already deployed at the target site TS. The physician will typically monitor the blood vessel with a fluoroscope to determine whether the vessel is completely occluded after coil 100 has been deployed (or to determine if recanalization has subsequently taken place). If the target site is not completely occluded, lumen occlusion system 2 will be used to apply radiofrequency energy to the coils at the target site to cause thermal damage to the luminal wall (this will induce a fibrogenic reaction). Of course, system 2 can also be utilized to deploy the initial coil 100 (or additions to the coil) at target site TS, as described in more detail in later embodiments.

Referring to FIG. 3A, the distal end 8 of catheter body 4 is introduced transluminally to a target site TS within a blood vessel BV or other body lumen. Typically, a guide wire (not shown) will first be introduced to the target site TS in a conventional manner. Note that positioner 10 may also be used as the guide wire, if desired, or positioner 10 may be used without the catheter if no additional coils are necessary. Once the guide wire is in position, the catheter body 4 will be introduced over the guide wire in a conventional "over-the-wire" manner until the distal end 8 of the body 14 is positioned slightly proximal of the vaso-occlusive coil 100, as shown in FIG. 3A.

After reaching the target site TS, positioner shaft 12 is advanced through catheter body 4 until jaws 16, 17 extend beyond distal end 8. Positioner shaft 12 will include an outer insulating sheath 102 proximal to the grasping end to protect the blood vessel wall from electrical energy delivered therethrough (discussed below). Jaws 16, 17 are opened by moving lever arm 26 (FIG. 1) in the distal direction, as described above. As shown in FIG. 3B, positioner shaft 12 will then be advanced distally until jaws 16, 17 contact a proximal portion of coil 100. As shown in FIG. 3C, jaws 16, 17 are preferably closed over a portion of coil 100 to establish electrical contact between the active electrodes (jaws 16, 17) and the coil and to ensure that this electrical contact remains intact during application of energy to the coil. A radiofrequency power supply 40 (FIG. 1) applies a radiofrequency voltage to jaws 16, 17 to initiate a radiofrequency current flow between the contiguous coil 100 and the return electrode 50. The radiofrequency power supply 40 may be optionally modified to provide an optimum impedance match. The radiofrequency current flows through coil 100, and the surrounding blood and the wall of blood vessel BV. The current thermally damages the blood vessel wall, causing localized swelling around the coil, as shown in FIG. 3C.

After maintaining the radiofrequency current flow for a desired time and at a desired current level, jaws 16, 17 will be opened to release coil 100. The positioner 12 is then withdrawn through catheter body 14. At the time of device removal, the blood vessel will be thrombosed and totally or mostly occluded. Subsequent fibrosis of the thrombus will make the occlusion substantially permanent.

Figure 4:
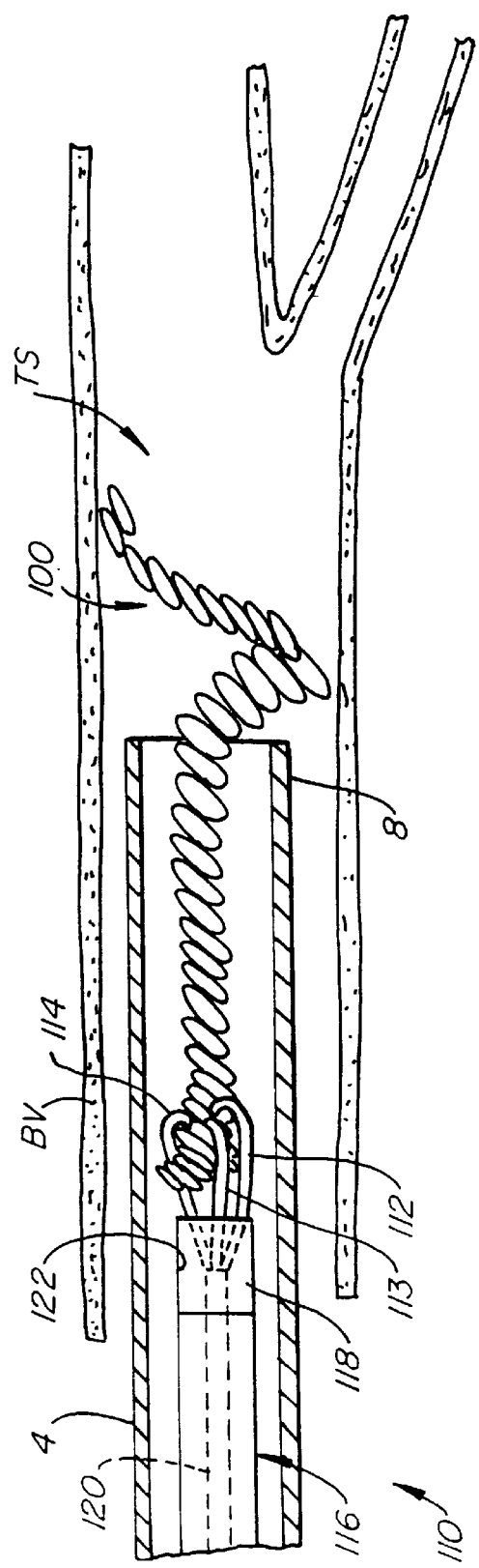
FIG. 4 is a sectional view of the distal portion of a second embodiment of a lumen occlusion device, illustrating a method of deploying or repositioning a vaso-occlusive coil in a body lumen.
Figure 5:
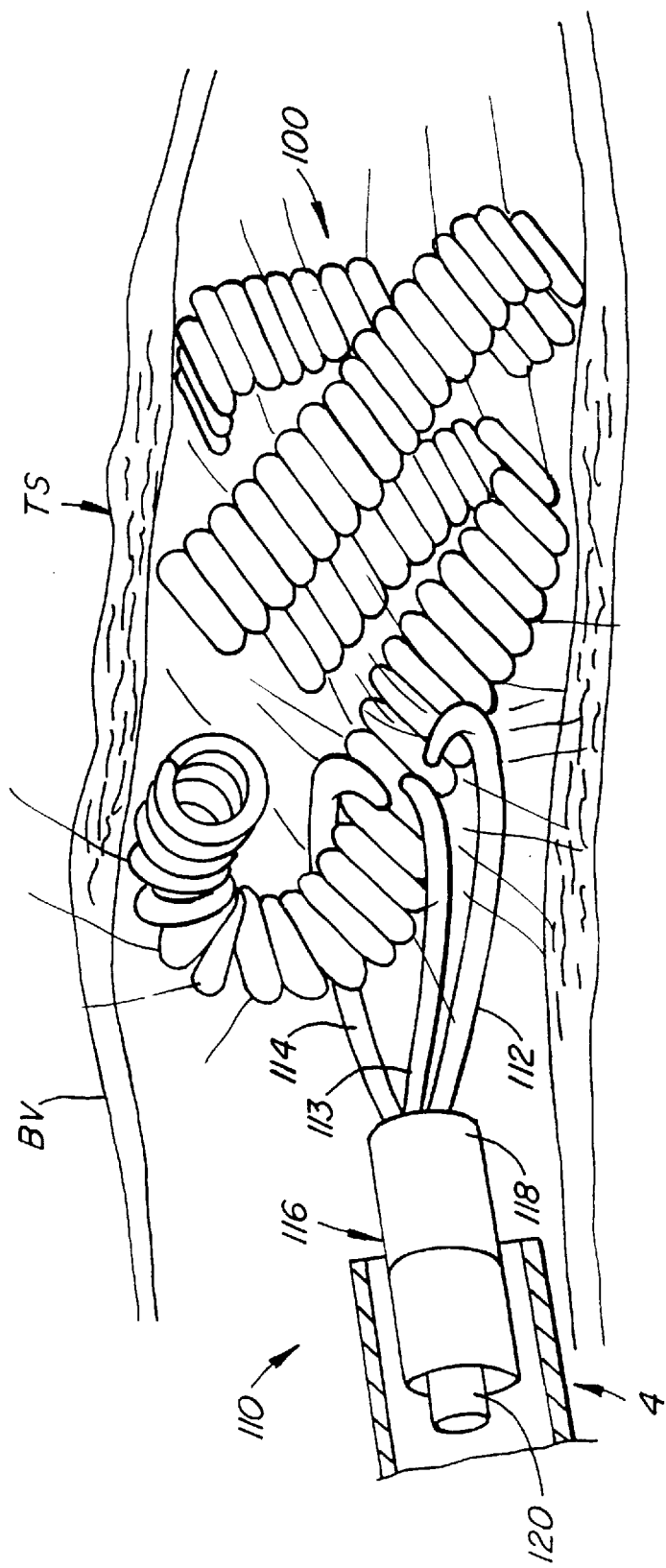
FIG. 5 is a detailed, cross-sectional view of the lumen occlusion device of FIG. 4, illustrating a plurality of coil-engaging elements releasably holding the vaso-occlusive coil.

A second embodiment 110 of the lumen occlusion system of the present invention is illustrated in FIGS. 4 and 5. System 110 is similar to system 2 in that it includes a proximal handle and an external, dispersive electrode coupled to an RF power supply (see FIG. 1). The system 110 differs from system 2, however, in that it includes a plurality of resilient hooks 112–114 for grasping vaso-occlusive coil 100 and delivering a radiofrequency current thereto. As shown in FIG. 4, a positioner shaft 116 has a proximal end (not shown) connected to the proximal handle, a distal end 118 and an axial lumen 119. An inner rod 120 is slidably positioned within axial lumen 119 and connected to an actuator mechanism (not shown) on the proximal handle.

Resilient hooks 112–114 are connected to the distal end of rod 118 and biased outward into a spaced apart configuration (not shown). When hooks 112–114 are completely or partially (FIGS. 4 and 5) withdrawn into shaft 116, the inner wall 122 of shaft 116 urges the hooks 112–114 towards each other. One or more of the hooks 112–114 is also an active electrode for delivering RF energy to coil 100. To that end, positioner shaft 116 includes an electrical conductor, such as a wire (not shown) extending through rod 118 to couple active electrode 112 with the RF power supply.

Occlusion system 110 can be used for deploying vaso-occlusive coil 100 at a target site TS in a blood vessel BV and for delivering radiofrequency energy to coil 100 to enhance fibrogenic occlusion of the target site TS. In use, hooks 112–114 are moved proximally outward beyond the distal end of positioner shaft 116 so that they are spaced apart from each other. The coil 100 is then positioned between hooks 112–114 and the hooks are partially withdrawn into shaft 116 so that the inner wall (not shown) of shaft 116 urges the hooks 112–114 together to grasp coil 100 (this partially withdrawn position is depicted in FIGS. 4 and 5). Positioner shaft 116 and coil 100 are then advanced through catheter body 4 to the target site (the distal end 8 of catheter body 4 is positioned at the target site as described previously). The inner wall 122 of cathetor body 4 facilitates the interlock between hooks 112–114 and coil 100 during movement through the catheter body.

Once coil 100 is advanced beyond the distal end 8 of catheter body 4, it will begin to relax into a convoluted configuration for occlusion of blood vessel BV, as shown in FIG. 4. Positioner shaft 116 is advanced until at least a portion of coil 100 or the entire coil and the hooks 112–114 extend beyond the distal end 8 of catheter body 4 (FIG. 5). An RF voltage is then delivered through active electrode or hooks 112–114 to the coil to generate thermal damage within blood vessel BV and induce subsequent fibrogenic occlusion of the blood vessel (as discussed previously). Since coil 100 is held in position by hooks 112–114, it will not migrate from TS during the occlusion process. Once the target site is damaged, localized swelling and thrombosis fixes coil 100 in place. Rod 120 is then moved distally to expand hooks 112–114 and release the coil 100. Rod 120 is typically biased proximally to a closed hook position. The positioner 116 and catheter 4 can then be removed from the patient's vasculature.

After the occlusion system has been removed from the blood vessel BV, a secondary RF treatment may become necessary if, for example, the target site is not sufficiently occluded. In this case, the occlusion system will be re-inserted as described above to re-access the occlusion coil 100, to recouple the coil to the RF electrode and to deliver additional RF energy to the target site.

Figure 6:
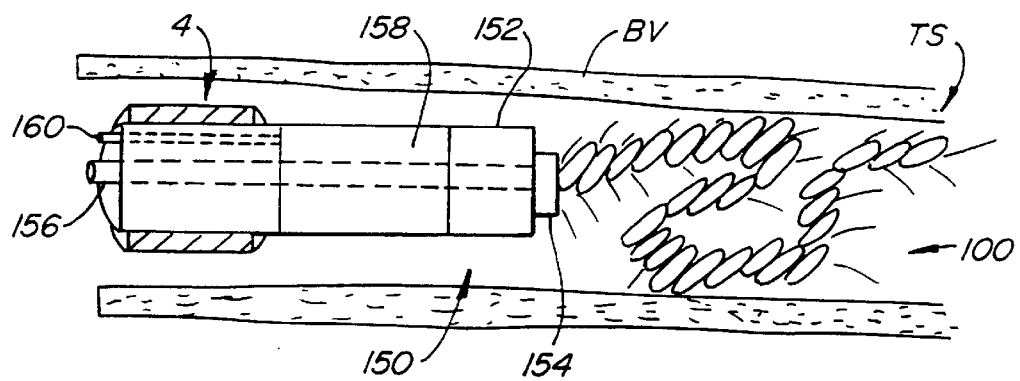
FIG. 6 is a partial sectional view of a third embodiment of a lumen occlusion device constructed in accordance with the principles of the present invention.
Figure 7:
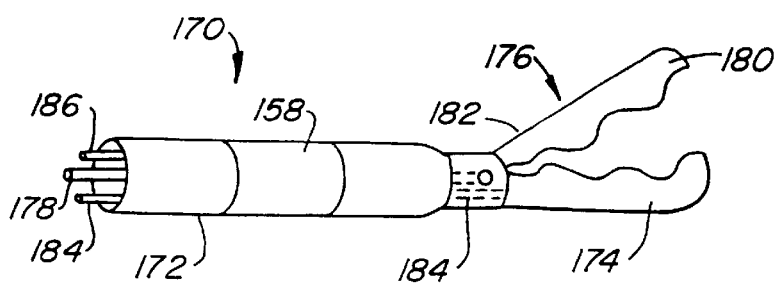
FIG. 7 is a partial sectional view of a portion of a lumen occlusion device according to another embodiment of the present invention.

FIGS. 6 and 7 illustrate bipolar embodiments of the present invention. Referring to FIG. 6, a positioner 150 comprises a flexible shaft 152 extending through catheter body 4 as in the previous embodiments. Positioner 150 includes one bipolar electrode in the form of a disc 154 disposed at the distal end of shaft 152. Disc 154 is electrically coupled to the RF power source by an inner conductive wire 156 extending through shaft 152. Shaft 152 is contained within an electrically conductive sheath proximal to its distal end to form a second electrode 158. Second electrode 158 is coupled to RF power source 40 by a second inner conductive wire 160 that extends through shaft 152 and is electrically insulated from wire 156. Note that second electrode 158 is schematically illustrated in FIG. 6 and may be larger than that shown. Second electrode 158 will preferably have a larger surface area than disc 154 and coil 100 to minimize tissue damage at the second electrode.

In use, positioner shaft 152 is advanced beyond the distal end of catheter body 4 so that active electrode disc 154 contacts the vaso-occlusive coil 100 deployed at the target site TS within blood vessel BV, as shown in FIG. 6. Electrode disc 154 may also be used as a pusher to deploy coil 100 by pushing the coil through catheter body 4. RF voltage is applied between electrode 158 and electrode 154 so that an RF current is initiated therebetween. Since the coil is more conductive than tissue, the RF current flows through at least a portion of coil 100. The surrounding blood and other fluids provide a path for the RF current from coil 100 and electrode 154 to electrode 158. The RF current will be sufficient to coagulate blood and to generate thermal damage to the intima of the tissue wall to enhance the occlusion of target site TS.

Referring to FIG. 7, another embodiment of positioner 170 comprises a shaft 172 and a pair of jaws 174, 176 extending from a distal end of shaft 170. Similar to previous embodiments, positioner 170 includes an inner rod 178 slidably disposed within shaft 172 and coupled to a proximal actuator (not shown) for opening and closing jaws 174, 176. In this embodiment, first jaw 174 and a distal portion 180 of second jaw 176 are the first electrodes. The second electrode 158 is disposed proximal to the first electrodes 174, 176, similar to FIG. 6. The jaws 174, 176 and second electrode 158 are each coupled to an RF power source by inner conducting elements 184, 186, respectively, which can comprise wires, rods or the like. RF voltage is applied between jaws 174, 176 and second electrode 158 to initiate RF current therebetween (via the coil).

Although the foregoing invention has been described in some detail by way of illustration and example, for purposes of clarity of understanding, it will be obvious that certain changes and modifications may be practiced within the scope of the appended claims.

What is claimed is:

1. A lumen occlusion system, comprising:
a source of high frequency electrical energy;
an introducer having a shaft with proximal and distal ends and an axial lumen therebetween;
a positioner disposed within the axial lumen and having a shaft and a distal engaging element for contacting a vaso-occlusive element at a target site within a body lumen, the distal engaging element comprising a first electrode coupled to the source of high frequency electrical energy; and
a second electrode coupled to the source of high frequency electrical energy
wherein the distal engaging element has an opened and closed configuration, and the positioner is slidable relative to the introducer to close the distal engaging element when the distal engaging element is unconfined outside the axial lumen of the introducer.

2. The system of claim 1 wherein the distal engaging element comprises means for advancing the vaso-occlusive element through the axial lumen of the introducer to a target site in a body lumen.

3. The system of claim 1 wherein the distal engaging element comprises a holding member for releasably holding a portion of a vaso-occlusive element.

4. The system of claim 1 wherein the holding member is configured to releasably hold the vaso-occlusive element beyond the distal end of the introducer.

5. The system of claim 1 wherein the second electrode comprises an external dispersive electrode adapted for engaging an external portion of the patient's body.

6. The system of claim 1 wherein the second electrode is a return electrode coupled to the introducer shaft, the return electrode being spaced from and electrically insulated from the first electrode.

7. The system of claim 1 wherein the first and second electrodes are located on the distal engaging element and the positioner shaft for initiating current therebetween.

8. The system of claim 1 wherein the introducer is a flexible shaft having dimensions suitable for introduction to a patient's vasculature.

9. The system of claim wherein the source of radiofrequency energy is configured to apply radiofrequency energy at a frequency of at least 200 kHz to the vaso-occlusive element.

10. A lumen occlusion system, comprising:
a source of high frequency electrical energy;
an introducer having a shaft with proximal and distal ends and an axial lumen therebetween;
a positioner disposed within the axial lumen and having a shaft and a distal engaging element for contacting a vaso-occlusive element at a target site within a body lumen, the distal engaging element comprising a first electrode coupled to the source of high frequency electrical energy; and
a second electrode coupled to the source of high frequency electrical energy;
wherein the distal engaging element comprises a plurality of opposed members movable between open and closed positions, at least one of the opposed members comprising the first electrode.

11. The system of claim 10 wherein the positioner further includes a proximal actuator for opening and closing the opposed members.

12. The system of claim 10 wherein the opposed members are biased towards each other.

13. A lumen occlusion device for use with a source of high frequency electrical energy comprising:
an introducer having a shaft with proximal and distal ends and an axial lumen therebetween;

a positioner slidably disposed within the axial lumen and having a distal engaging element for releasably engaging an electrically conductive vaso-occlusive element at a target site within a body lumen, the distal engaging element comprising an electrode; and an electrical conductor for coupling the electrode to the source of high frequency electrical energy wherein the distal engaging element has an opened and closed configuration, and the positioner is slidable relative to the introducer to close the distal engaging element when the distal engaging element is unconfined outside the axial lumen of the introducer.

14. The device of claim 13 wherein the distal engaging element comprises means for releasably holding the vaso-occlusive element in contact with the electrode beyond the distal end of the introducer.

15. The device of claim 13 wherein the distal engaging element comprises a distal surface sized to engage the vaso-occlusive element and to push said element through the axial lumen of the introducer, the vaso-occlusive element being released from the distal surface of the engaging element when the vaso-occlusive element is pushed beyond the distal end of the introducer shaft.

16. The device of claim 13 wherein the distal engaging element comprises a plurality of opposed elements movable between open and closed positions, at least one of the opposed elements comprising the first electrode.

17. The system of claim 16 wherein the positioner further comprises a proximal actuator for opening and closing the opposed elements.

18. The system of claim 16 wherein the opposed elements are biased towards each other.

19. The device of claim 13 wherein the introducer is a flexible catheter.

* * * * *